United States Patent [19]

Quisno

[11] 4,450,844
[45] May 29, 1984

[54] PATCH SYSTEM FOR USE ON THE SKIN
[75] Inventor: Robert A. Quisno, Monroe, Ohio
[73] Assignee: Hill Top Research, Inc., Cincinnati, Ohio
[21] Appl. No.: 324,048
[22] Filed: Nov. 23, 1981
[51] Int. Cl.³ .............................................. A61B 10/00
[52] U.S. Cl. .................................................... 128/743
[58] Field of Search .................. 128/132 R, 153, 154, 128/155, 156, 165, 630, 743; 604/46, 47, 332

[56] References Cited

U.S. PATENT DOCUMENTS 4,158,359  6/1979  Kurokawa et al. ................ 128/630

FOREIGN PATENT DOCUMENTS 8100199  2/1981  European Pat. Off. ........... 128/743
2420345  11/1975  Fed. Rep. of Germany ...... 128/743
915591  9/1965  U.S.S.R. .............................. 128/743

Primary Examiner—Richard J. Apley
Assistant Examiner—Harry J. Macey
Attorney, Agent, or Firm—Frost & Jacobs

[57] ABSTRACT

A patch system for use on the skin of a human or animal subject for predictive testing, diagnostic testing and to serve as a dermal delivery system for drugs. The patch system comprises an open, one-piece, inverted dish-shaped housing of non-toxic, inert, soft and flexible material. About its periphery the chamber terminates in a pair of parallel, spaced, continuous skin-contacting edges. The housing may contain an absorbent pad. The housing is mounted on a piece of adhesive coated tape by which it is affixed to the skin. Prior to use, the adhesive tape and the housing of the patch system may be provided with a protective release paper.

11 Claims, 13 Drawing Figures

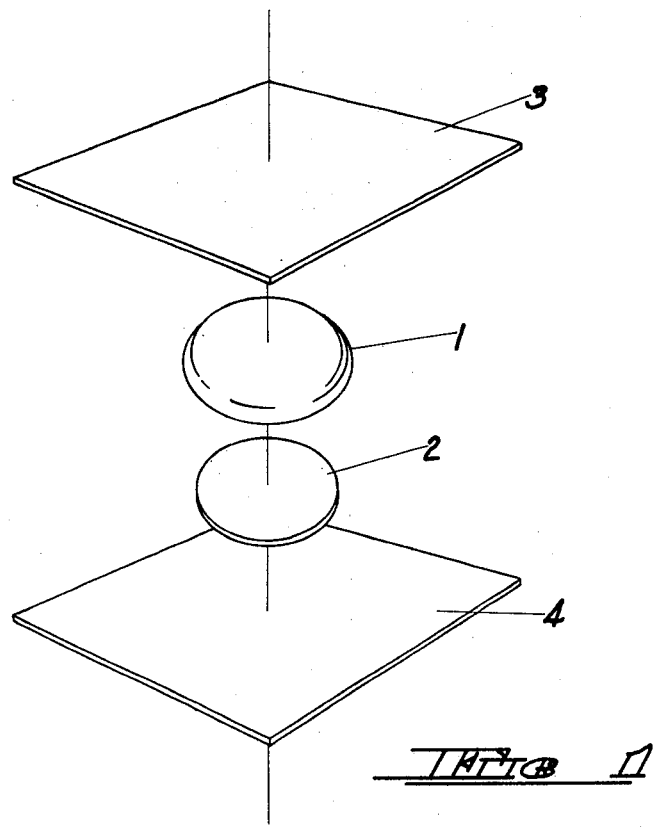
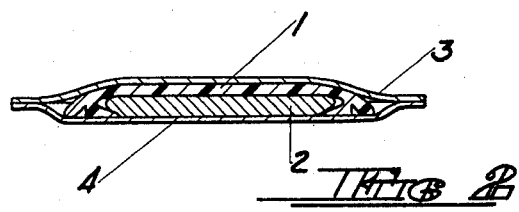

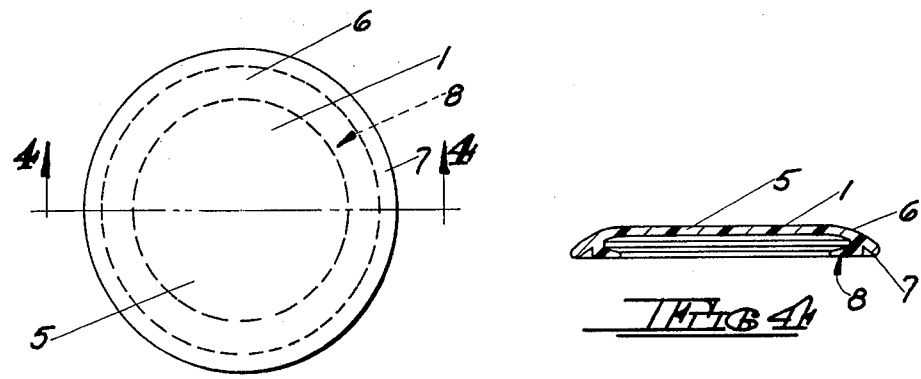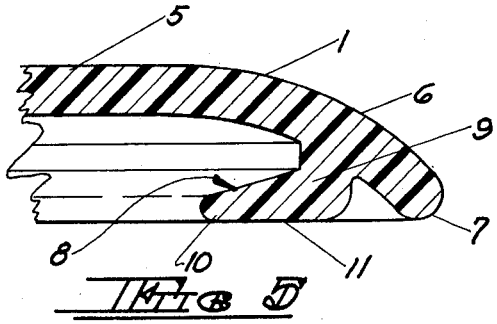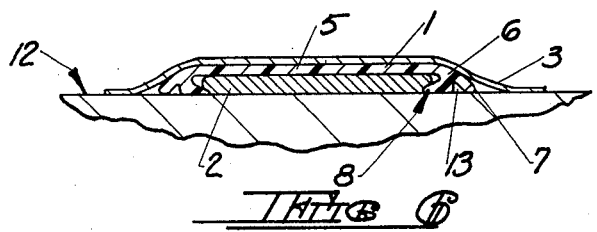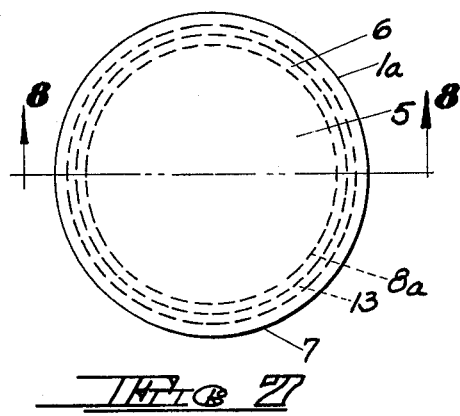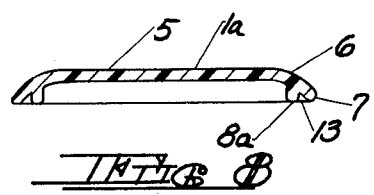

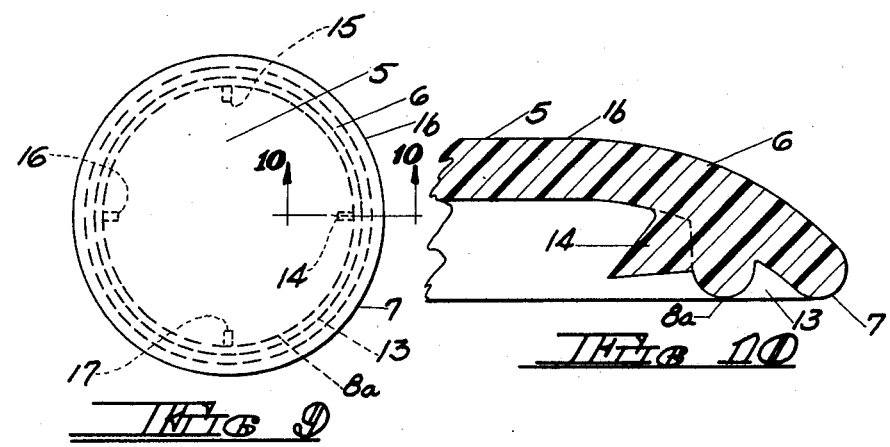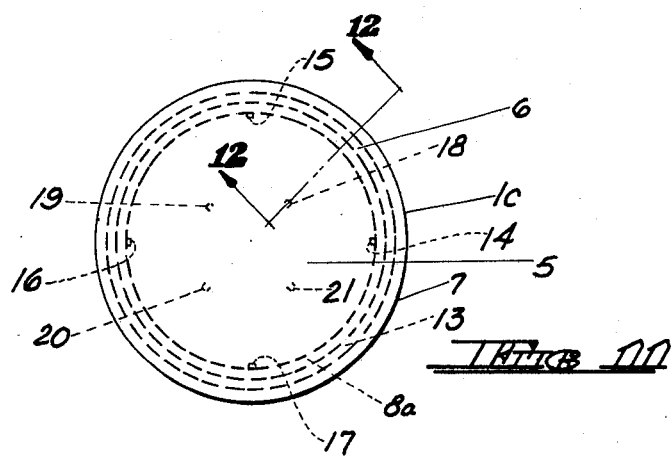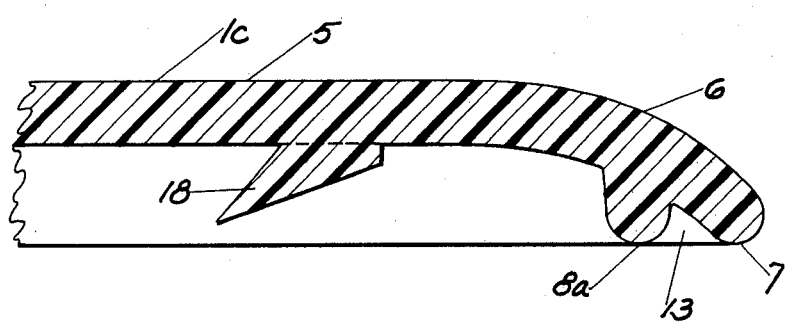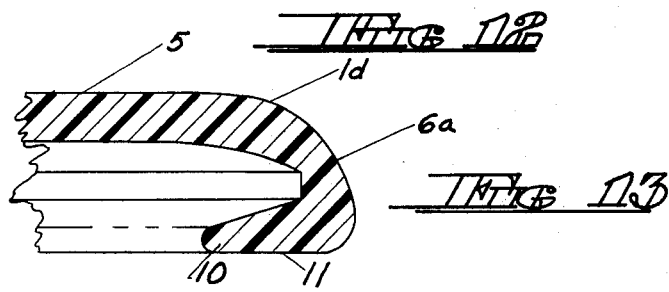

PATCH SYSTEM FOR USE ON THE SKIN

TECHNICAL FIELD

The invention relates to a patch system for use on the skin of a human or animal subject, and more particularly to a patch system utilizing an open, one-piece, inverted dish-shaped housing of non-toxic, inert, soft and flexible material, terminating at its periphery in a pair of integral, parallel, spaced, continuous skin-contacting edges.

BACKGROUND ART

Prior art workers have devised numerous types of patch systems. In their simplest form, prior art patch systems comprised absorbent patches of woven or non-woven synthetic or natural fibers affixed directly to an adhesive tape and, in many instances, protected by release papers. In similar structures, an impervious layer cellophane, or the like, was located between the patch and the adhesive tape. In many of these prior art structures, the sample material applied to the patch system came into contact with the tape. Many of these systems were limited as to the type of tape which could be used and frequently, the tape would not adhere well, particularly in the presence of water, perspiration, or the like. Often the tape was more irritating and would gap easily so that the patch system was non-occlusive. The sample material applied to such structures would frequently dry out rapidly.

In an attempt to provide a more occlusive patch system and to prevent the sample from being in contact with the tape, prior art workers have developed various types of small, dish-like housings having a continuous skin-contacting edge. These housings have generally been made of metal such as aluminum and the like. These structures, however, have been characterized by certain disadvantages such as being rigid, too thick and having limited sample volume. A recent example of such structures is taught in U.S. Pat. No. 4,158,359. This patent teaches a single or multi-piece housing containing an absorbent pad and having peripheral edges which are turned inwardly or outwardly so as to form a continuous seal with the skin. One embodiment of this patent comprises a housing having outwardly rolled edges with an additional annular member adapted to form a second seal and to retain an absorbent pad within the housing. The housing of this patent is affixed to an adhesive covering sheet and is surrounded by an annular porous protecting sheet. The housing of this reference has a limited sample volume and is generally rigid, being made of metal or a synthetic resin.

The present invention is directed to a patch system intended to overcome the deficiencies of prior art patch systems and to be substantially completely occlusive to render tests, for example, more sensitive and reproducible. This is accomplished by means of a pair of integral parallel, spaced, continuous, skin-contacting edges of the housing having an air space therebetween, and by virtue of the fact that the housing is made of soft and flexible material.

The sample material applied by way of the patch system does not contact the adhesive of the tape which mounts the housing and different types of tape can be used, such as hypoallergenic tapes.

The housing, which is made of non-toxic, inert material, provides good sample retention for at least 48 hours and can be used with or without an absorbent pad. Various sizes of absorbent pads can be used and the system permits modifications of patch testing procedures not possible with prior art systems.

The patch system works well even in the presence of perspiration and one to whom the patch system is applied can swim and shower. When used for test purposes, the patch system (with sample applied) can be prepared ahead of time, in the laboratory and taken to the test site, ready for use. The patch system of the present invention provides a technique which may reduce the number of visits for panelists during testing. The system further enables measurement of the amount of sample before and after application to a panelist, which is useful in controlled investigations of new drugs. Finally, the system can be used as single patches or made into strips containing a plurality of housings.

The patch system of the present invention has numerous applications. For example, it can be used in conventional predictive patch testing and in diagnostic testing (for example, by dermatologists and allergists to determine what is the causative agent for a patient's skin reaction). The patch system can also be used as a dermal drug delivery vehicle. The housing will hold sufficient drug to allow it to be gradually absorbed through the skin for certain treatments such as an anesthetic patch for a painful procedure. The patch system is suitable for use both with humans and animals.

DISCLOSURE OF THE INVENTION

According to the invention there is provided a patch system for use on the skin of a human or animal subject for predictive testing, diagnostic testing, drug delivery and the like.

The patch system comprises an open, one-piece, inverted dish-shaped housing of non-toxic, inert, soft and flexible material. About its periphery, the housing terminates in a pair of integral parallel, spaced, continuous, skin-contacting edges. The housing may contain an absorbent pad, if desired.

In a preferred embodiment of the present invention, the outer skin-contacting edge of the housing is beaded or rounded, providing a rounded sealing surface. The inner edge is flattened and provided with an annular flange-like portion extending inwardly of the housing so as to provide a wide, flat sealing surface. The sealing surfaces of both the inner and outer edges are substantially coplanar. The annular flange-like portion of the inner edge also serves as a retaining means for an absorbent pad, if used.

In a second embodiment, both the inner and outer edges are beaded or rounded, providing rounded, substantially coplanar sealing surfaces. A third embodiment differs from the second embodiment only in that a plurality of inwardly extending spikes are provided in association with the inner edge, evenly spaced thereabout, to retain an absorbent pad within the housing. Finally, a fourth embodiment is similar to the third embodiment, differing only in that additional inwardly extending spikes are provided on the inside surface of the housing, itself, spaced inwardly from the inner edge and its associated spikes, to further assist in retaining an absorbent pad within the housing.

While the housing in some applications may be used alone (with or without an absorbent pad), in most applications it will be affixed to the skin by a piece of adhesive coated tape. To this end, the chamber may be adhered to the tape with its open face facing away from the tape. Prior to use, the adhesive tape and the chamber of the patch system may be protected with a removable release paper.

It would also be within the scope of the invention to provide a housing similar to the above described preferred embodiment but with the outer skin-contacting edge of the housing eliminated as will be described hereinafter.

BRIEF DESCRIPTION OF THE DRAWINGS

FIG. 1 is an exploded perspective view of the patch system of the present invention.

FIG. 2 is a cross sectional view of the patch system of FIG. 1 in assembled condition.

FIG. 3 is a top plan view of the housing of FIG. 1.

FIG. 4 is a cross sectional view taken along section line 4—4 of FIG. 3.

FIG. 5 is an enlarged, fragmentary, cross sectional view of the sealing edges of FIG. 4.

FIG. 6 is a fragmentary cross sectional view illustrating the structure of FIGS. 1 and 2 mounted on the skin of a subject.

FIG. 7 is a top plan view of another embodiment of the housing of the present invention.

FIG. 8 is a cross sectional view taken along the section line 8—8 of FIG. 7.

FIG. 9 is a top plan view of another embodiment of the housing of the present invention.

FIG. 10 is an enlarged, fragmentary, cross sectional view taken along section line 10—10 of FIG. 9.

FIG. 11 is a top plan view of yet another embodiment of the housing of the present invention.

FIG. 12 is an enlarged, fragmentary, cross sectional view taken along section line 12—12 of FIG. 11.

FIG. 13 is an enlarged fragmentary cross sectional view of the modification of the embodiment of FIGS. 1 through 6.

DETAILED DESCRIPTION OF THE INVENTION

Throughout this description, like parts have been given like index numerals. Reference is first made to FIGS. 1 and 2 wherein the patch system of the present invention is illustrated in its most complete form. The patch system comprises a sample-retaining housing 1 and an absorbent pad 2, adapted to be mounted in the housing 1. In most applications, the housing 1 is retained in position on the skin by an adhesive coated cover sheet 3. Prior to use, the housing 1, absorbent pad 2 and cover sheet 3 are protected by a release paper 4.

The housing 1 can be made of any appropriate soft and flexible material which is substantially non-toxic and inert. The housing lends itself well to being molded of a plastic material. For example, the polyethylene vinyl acetate group of plastics can be used. As a non-limiting example, excellent results have been achieved with U.E. 634-00 Ethylene vinyl acetate copolymer, sold under the trademark Ultrathene by United States Industrial Chemicals of Cincinnati, Ohio. This material is inert, very pure, non-toxic, contains no plasticizers and demonstrates no tendency to be leachable.

The absorbent pad 2 may be made of an appropriate material safe for use adjacent to the skin and compatible with the sample to be applied to the pad. With these limitations in mind, the pad may be made of a spongy or foamed plastic material, paper, or woven or nonwoven synthetic or natural fibers. Excellent results have been achieved, for example, with a nonwoven cotton swatch sold under the trademark Webril by Kendall Company of Wellesley Hill, MA.

The samples or drugs to be applied to the skin by means of the patch system of the present invention may be in various forms such as liquids, solids, pastes, powders and the like. In the case of solids, semi-solids, powders and the like, it may be desirable to dispense with the absorbent pad 2, filling the housing 1 directly with the sample.

The cover sheet 3 is normally made of a tape, coated on one side with a pressure-sensitive adhesive. In the patch system of the present invention, the cover sheet 3 may be made of any appropriate adhesive tape which is non-irritating to the skin. Selection of an appropriate adhesive tape will be made on the basis of the nature and purpose of the application of the patch system and the conditions thereof. For example, the tape can be a plastic film tape, a fabric tape, a paper tape, or the like. Excellent results have been achieved, for example, using a fabric based adhesive tape sold under the trademark Durapore by 3M Company of St. Paul, Minn., and a paper based tape sold under the trademark Scanpor by Norgesplaster of As, Norway. It has been found that paper tapes tend to channel more than fabric tapes. These channels allow moisture to move along them by capillary action and thus allow more moisture to pass into the housing 1 than do fabric tapes which do not wrinkle as much. Nevertheless, both tapes perform well under conditions of showering and swimming. Both tapes demonstrate good adhesion properties in the presence of perspiration.

The release paper 4 can again be of any appropriate type, suitable for use with the particular application to which the patch system is directed. Excellent results have been achieve, for example, utilizing a paper coated with polyethylene silicone. A specific example is 63# BL Polysilk ® L275, sold by H. P. Smith Paper Company of Chicago, Ill. In some applications of the patch system of the present invention, particularly in its use as a drug delivery means and in its application to animals, it may be desirable to dispense with the cover sheet paper 3 and release paper 4.

Reference is now made to FIGS. 3, 4 and 5 which illustrate the preferred embodiment of the housing 1. The housing 1 comprises an integral, one-piece, molded structure of an inverted, circular, dish-shaped configuration. The housing has a substantially planar central body portion 5. Near its periphery, the housing 1 has a portion 6 which curves downwardly and outwardly. The portion 6 terminates in a beaded or rounded edge 7. The rounded edge 7 constitutes the outer skin-contacting edge. A second or inner skin-contacting edge is generally indicated at 8. As is most clearly shown in FIG. 5, the skin-contacting edge 8 comprises a first portion 9 which depends downwardly from the inner surface of the curved portion 6. The portion 9 terminates in a laterally and inwardly extending, annular flange-like portion 10. As can be seen in FIGS. 3 and 6, the flange-like portion 10 serves as a retaining means for the absorbent pad 2 (when used). The annular flange-like portion 10 also provides a surface 11 constituting a skin-contacting and sealing surface. It will be apparent from FIG. 5 that that portion of the outer edge 7 which contacts the skin and the surface 11 of the inner edge 8 are substantially coplanar. It has been found that the housing 1, by virtue of its soft and flexible nature and its outer skin-contacting edge 7 and inner skin-contact edge 8, provides a patch system of excellent occlusive properties.

The embodiment of housing 1 illustrated in FIGS. 3 through 5, and those embodiments (to be described hereinafter) illustrated in FIGS. 7 through 12 have been shown as having an overall circular configuration. While this overall configuration is preferred, the housing is not intended to be so limited. The housing could have an overall configuration which is square, rectangular, triangular, hexagonal or the like. So long as the housing is made of soft and flexible material and is provided with a pair of parallel, spaced, continuous, skin-contacting edges, as taught herein, the improved characteristics of the present invention will be achieved.

Reference is now made to FIG. 6 wherein the embodiment of FIGS. 1 through 5 is shown applied to the skin, generally indicated at 12. In use, the release paper 4 is removed and the sample to be administered or tested is applied to the absorbent pad 2. As indicated above, under some circumstances the sample is applied directly to the housing 1, the pad 2 being eliminated. Once the sample has been applied to the patch system, the patch system is applied directly to the surface of the skin 12. Again, it will be remembered that the sample can be applied to the patch system ahead of time and a release paper applied. The release paper is thereafter removed at the time of use.

It will be evident from FIG. 6 that the body portion 5 of the housing is spaced from the skin 12 by the curved portion 6 and skin-engaging edges 7 and 8. The sample is maintained out of contact with the cover sheet or tape 3 by the housing 1. Furthermore, the housing 1 assures that the tape 3 contacts the skin at an adequately spaced distance from the area of contact between the skin and the sample. A highly occlusive structure is achieved by virtue of the soft and flexible nature of housing 1 and the two continuous peripheral sealing edges 7 and 8 with and air space 13 therebetween.

A second embodiment of the housing of the present invention is illustrated in FIGS. 7 and 8. In these Figures, the housing is indicated at 1a. The housing 1a is substantially identical to the housing 1 of FIGS. 3 through 5, with the exception of the configuration of the inner sealing edges. As a result of this, like parts have been given like index numerals. Thus, the housing has a substantially planar body portion 5, curved body portion 6, outer sealing edge 7. The inner sealing edge 8a is again uniformly inset from the outer sealing edge 7 with an air space 13 therebetween. The inner sealing edge 8a constitutes a flange which depends downwardly from the inside surface of the housing portion 6. The lowermost end of the inner sealing edge 8a is beaded or rounded in the same manner as is the outer edge 7. It will be noted that once again the sealing surfaces of the edges 7 and 8a are substantially coplanar. The use of the housing 1a is identical to that described with respect to housing 1.

Another embodiment of the housing of the present invention is illustrated in FIGS. 9 and 10. In these Figures the housing is indicated at 1b. The housing 1b is substantially identical to the housing 1a of FIGS. 7 and 8, and again like parts have been given like index numerals. The embodiment 1b of the housing differs from the embodiment 1a only in the provision of a plurality of spikes. One such spike is shown at 14 in FIG. 10. The spike 14 constitutes an integral, one-piece part of the housing structure. The spike is directed inwardly of the housing and its purpose is to engage and retain the absorbent pad 2 (see FIG. 1), when used. The housing 1b will be provided with a plurality of such spikes evenly spaced along the inner sealing edge 8a. While the number of such spikes does not constitute a limitation on the present invention, it has been found that four such spikes will generally serve the purpose. Four spikes are shown in broken lines at 14 through 17 in FIG. 9.

Yet another embodiment of the housing of the present invention is illustrated at 1c in FIGS. 11 and 12. The embodiment 1c is identical to the embodiment 1b and again like parts have been given like index numerals. Thus, the embodiment 1c has a substantially planar body portion 5, a downwardly and outwardly curved portion 6, sealing edge portions 7 and 8a separated by air space 13 and a first set of inwardly directed spikes 14 through 17. The embodiment 1c differs from the embodiment 1b in that a second set of inwardly directed spikes is provided. Such a spike is shown at 18 in FIG. 12. The spike 18 is spaced inwardly from the inner sealing edge 8 and depends downwardly from the inside surface of the planar portion 5. The pointed end of spike 18 extends inwardly of the structure.

The purpose of spike 18 is to serve as an additional means to engage and retain the absorbent pad 2 (see FIG. 1). To this end, a plurality of such spikes are provided. While the number of such spikes is not a limitation on the present invention, FIG. 11 illustrates four such spikes, evenly spaced about the center of the structure, at 18 through 21 and offset 45° with respect to the spikes 14 through 17. In all other respects, the use of the embodiment 1c is identical to that described with respect to the embodiment 1.

FIG. 13 illustrates another embodiment of housing, generally indicated at 1d. The housing 1d is substantially identical to housing 1 of FIGS. 1 through 6, differing only in that the outer skin-contacting edge 7 has been eliminated. Thus, the housing 1d comprises an integral, one-piece, molded structure of an inverted, circular dish-shaped configuration. The housing has a substantially planar central portion 5. Near its periphery, the housing 1d has a portion 6a which curves downwardly and outwardly and which terminates in a laterally and inwardly extending, annular flange-like portion 10. The portion 10 has a relatively wide, flat, annular skin-contacting surface 11. The portion 10 can also serve as a retaining means for an absorbent pad (not shown), if desired. The use of the housing 1d and the material from which it is made are the same as described with respect to the embodiment 1 of FIGS. 1 through 6.

The housings of the present invention are re-usable under many circumstances. Absorbent pads 2 of various diameters can be used in the same housing. It is also within the scope of the invention to produce the housing of the present invention in various sizes.

While dimensions are not intended to constitute a limitation of the present invention, excellent results have been achieved with the patch system of the present invention wherein the housing 1 had an overall diameter of one inch and an overall height or thickness of one-sixteenth inch. The absorbent pad 2 had a diameter of three-quarters of an inch. The cover sheet or adhesive tape 3 was of square configuration having a dimension of one and three-quarter inches on a side, while the release paper was of square configuration having a length of two inches per side.

In the above description and in the claims, the housing and its parts are described using such words and phrases as "inverted", "downwardly", "downwardly and outwardly", and the like. It will be understood that such words and phrases are used for purposes of explanation and clarity and are used in conjunction with the Figures. In use, the housing may be placed in, or may assume, any appropriate orientation.

Modifications may be made in the invention without departing from the spirit of it.

What is claimed is:

1. A patch system for use on skin for predictive testing, diagnostic testing and dermal drug delivery, said patch system comprising an open-faced, integral, one-piece housing of non-toxic, inert, soft and flexible material, said housing having a substantially planar central body portion terminating in a peripheral body portion of substantially arcuate cross section curving outwardly and downwardly below said central body portion, said peripheral body portion terminating in an outer skin-contacting edge, an inner skin-contacting edge depending downwardly from said peripheral body portion, said skin-contacting inner and outer edges being parallel and spaced from each other and each being continuous, said skin-contacting inner and outer edges being coplanar, being the only skin-contacting portions of said housing, and having an air space therebetween.

2. The structure claimed in claim 1 including an absorbent pad located within said housing.

3. The structure claimed in claim 2 including a cover sheet comprising a piece of tape coated on one of its surfaces with a pressure sensitive adhesive, said central body portion of said housing being affixed to said adhesive-coated surface of tape with said skin-contacting edges facing away therefrom.

4. The structure claimed in claim 1 including a cover sheet comprising a piece of tape coated on one of its sides with a pressure sensitive adhesive, said central body portion of said housing being affixed to said adhesive-coated side of said tape with said skin-contacting edges facing away therefrom.

5. The structure claimed in claim 4 including a removable release paper covering said housing and said adhesive-coated surface of said tape.

6. The structure claimed in claim 1 wherein said housing is circular in configuration.

7. The structure claimed in claim 1 wherein said outer skin-contacting edge of said peripheral body portion is of rounded configuration, said inner skin-contacting edge comprising a first downwardly depending portion and a second annular flange-like portion extending inwardly of said housing and away from said outer skin-contacting edge, said annular flange-like portion having a flat skin-contacting surface substantially coplanar with said outer skin-contacting edge.

8. The structure claimed in claim 7 including an absorbent pad located within said housing, said annular flange-like portion of said inner skin-contacting edge engaging and retaining said pad within said housing.

9. The structure claimed in claim 4 including a cover sheet comprising a piece of tape coated on one of its sides with a pressure sensitive adhesive, said central body portion of said housing being affixed to said adhesive-coated side of said tape with said skin-contacting edges facing away therefrom.

10. The structure claimed in claim 9 including a removable release paper covering said housing and said adhesive-coated side of said tape.

11. The structure claimed in claim 4 wherein said housing is circular in configuration.

* * * * *